(12) United States Patent
Morita et al.

(10) Patent No.: US 9,848,601 B2
(45) Date of Patent: Dec. 26, 2017

(54) PESTICIDAL COMPOSITION, AND METHOD FOR CONTROLLING PESTS

(75) Inventors: Masayuki Morita, Osaka (JP); Takao Awazu, Kusatsu (JP); Akira Nakagawa, Kusatsu (JP); Mitsugu Iwasa, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 931 days.

(21) Appl. No.: 12/935,289

(22) PCT Filed: Apr. 10, 2009

(86) PCT No.: PCT/JP2009/057394
§ 371 (c)(1),
(2), (4) Date: Sep. 29, 2010

(87) PCT Pub. No.: WO2009/128409
PCT Pub. Date: Oct. 22, 2009

(65) Prior Publication Data
US 2011/0028521 A1    Feb. 3, 2011

(30) Foreign Application Priority Data
Apr. 17, 2008    (JP) .................. 2008-107804

(51) Int. Cl.
*A01N 43/40*    (2006.01)
*A01N 43/80*    (2006.01)
(52) U.S. Cl.
CPC ............. *A01N 43/40* (2013.01); *A01N 43/80* (2013.01)
(58) Field of Classification Search
IPC ............................................ A01N 43/40,25/30
See application file for complete search history.

(56) References Cited

U.S. PATENT DOCUMENTS

| | | | |
|---|---|---|---|
| 5,228,895 A * | 7/1993 | Kelly et al. ............. | 71/63 |
| 5,360,806 A | 11/1994 | Toki et al. | |
| 6,375,965 B1 | 4/2002 | Matsuo et al. | |
| 2002/0142021 A1 | 10/2002 | Matsuo et al. | |
| 2005/0004368 A1 | 1/2005 | Mio et al. | |
| 2005/0255171 A1 | 11/2005 | Matsuo et al. | |

FOREIGN PATENT DOCUMENTS

| | | | |
|---|---|---|---|
| EP | 0 580 374 | 1/1994 | |
| JP | 6 321903 | 11/1994 | |
| JP | 11 5706 | 1/1999 | |
| WO | 02 34050 | 5/2002 | |
| WO | WO 02/37964 A1 | 5/2002 | |
| WO | 03 044013 | 5/2003 | |
| WO | WO 2005/104846 A1 | 11/2005 | |
| WO | WO 2006/038019 * | 4/2006 | ............. A01N 25/30 |
| WO | WO 2006/045522 A1 | 5/2006 | |
| WO | WO 2007/017502 A2 | 2/2007 | |
| WO | WO 2007/017502 A3 | 2/2007 | |

OTHER PUBLICATIONS

International Search Report dated Jun. 16, 2009 in PCT/JP09/57394 filed Apr. 10, 2009.
Combined Chinese Office and Search Report dated Oct. 23, 2012, in Patent Application No. 200980113459.X (with English-language translation).
Xiaoyi Wang, et al., "Application of Surfactants to Pesticides and Their Pesticidal Potency-Enhancing Mechanism", Translated Collection of Pesticide, No. 4, Dec. 31, 1997, pp. 52-57.
Gao Congfen, et al., "A Review on the Synergism of Insecticide", Acta. Univ. Agric. Boreali-Occidentalis, vol. 24, No. 1, Feb. 29, 1996, pp. 88-92 (with English Abstract).
Extended European Search Report dated Nov. 20, 2012 in European Patent Application No. 09732648.2.
Tong-Xian Liu, et al., "Insecticidal activity of surfactants and oils against silverleaf whitefly (*Bemisia argentifolii*) nymphs (Homoptera: Aleyrodidae) on collards and tomato", Pest Management Science, vol. 56, No. 10, XP007919318, Oct. 10, 2000, pp. 861-866.
R. S. Cowles, et al., ""Inert" Formulation Ingredients with Activity: Toxicity of Trisiloxane Surfactant Solutions to Twospotted Spider Mites (Acari: Tetranychidae)", J. Econ. Entomol., vol. 93, No. 2, XP55043761, Jan. 1, 2000, pp. 180-188.
Alan Knowles, "New Developments in Crop Protection Product Formulation", Agrow Reports, T&F Informa UK Ltd., XP055043937, May 2005, pp. 177- 224 (plus cover page).

* cited by examiner

Primary Examiner — Kortney L. Klinkel
(74) Attorney, Agent, or Firm — Oblon, McClelland, Maier & Neustadt, L.L.P.

(57) ABSTRACT

To provide a pesticidal composition having a stable and high pesticidal effect. The pesticidal composition comprises a pyridine compound represented by the formula (I):

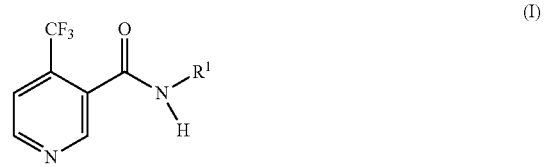

(I)

(wherein $R^1$ is $CH_2CN$ or

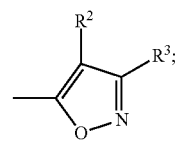

and each of $R^2$ and $R^3$ which are independent of each other, is a hydrogen atom, a halogen atom, $C_{1-6}$ alkyl or $C_{1-6}$ alkoxy) or its salt and at least one potency-enhancing component selected from the group consisting of a nonionic surface active agent, an anionic surface active agent, a cationic surface active agent, an amphoteric surface active agent, an animal or plant oil, a mineral oil, a water-soluble polymer, a resin and a wax.

4 Claims, No Drawings

PESTICIDAL COMPOSITION, AND METHOD FOR CONTROLLING PESTS

TECHNICAL FIELD

The present invention relates to a pesticidal composition having remarkably improved pesticidal effects, particularly insecticidal and miticidal effects, and a method for controlling pests by using such a composition.

BACKGROUND ART

N-cyanomethyl-4-trifluoromethyl-3-pyridinecarboxyamide (common name: flonicamid) belonging to the compound represented by the after-mentioned formula (I) is a compound disclosed as compound No. 1 in Patent Document 1 and is an active ingredient for a pesticide. Further, compounds other than flonicamid, which belong to the compound represented in the after-mentioned formula (I) are compounds disclosed in Patent Document 2. Patent Document 3 discloses a pesticide having flonicamid and another pesticide combined. However, the composition of the present invention having the compound represented by the following formula (I) and a specific potency-enhancing component combined, has not been known.

Prior Art Documents

Patent Documents

Patent Document 1: European Patent Publication No. 580374

Patent Document 2: WO03/044013

Patent Document 3: European Patent Publication No. 1328154

SUMMARY OF THE INVENTION

Problems to be Solved by the Invention

Conventional pesticides have respectively characteristic spectrums and effects, but have some problems that the effects are sometimes unsatisfactory to certain pests, that their residual activities are sometimes poor and the effects are not satisfactorily maintained for a certain period of time, and that satisfactory pesticidal effects can not be practically achieved depending on applications. Also, even if there are some pesticides excellent in their pesticidal effects, they are demanded to be improved in respect of safety to fishes, crustacean and domestic animals and are also demanded to achieve a high pesticidal effect at a small dosage.

Means to Solve the Problems

The present inventors have conducted a study to solve the above problems and as a result, have found it possible to obtain an unexpectedly excellent pesticidal effect when a specific potency-enhancing component is added at the time of applying the compound represented by the after-mentioned formula (I) or its salt, as compared with a case where no such component is added, and thus, the present invention has been accomplished.

That is, the present invention relates to a pesticidal composition comprising a pyridine compound represented by the formula (I):

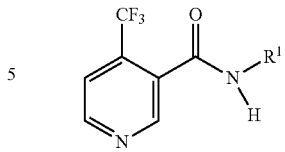
(I)

(wherein $R^1$ is $CH_2CN$ or

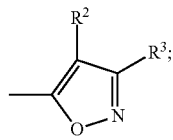

and each of $R^2$ and $R^3$ which are independent of each other, is a hydrogen atom, a halogen atom, $C_{1-6}$ alkyl or $C_{1-6}$ alkoxy) or its salt, and at least one potency-enhancing component selected from the group consisting of a nonionic surface active agent, an anionic surface active agent, a cationic surface active agent, an amphoteric surface active agent, an animal or plant oil, a mineral oil, a water-soluble polymer, a resin and a wax. Further, the present invention relates to a method for controlling pests, which comprises applying such a pesticidal composition to pests.

Advantageous Effects of the Invention

The pesticidal composition of the present invention is one having a stable and high pesticidal effect, and it is possible to control pests by using such a composition.

BEST MODE FOR CARRYING OUT THE INVENTION

"$C_{1-6}$ alkyl" in the formula (I) is linear or branched alkyl having from 1 to 6 carbon atoms, preferably linear or branched alkyl having from 1 to 4 carbon atoms ($C_{1-4}$ alkyl) more preferably alkyl having 1 or 2 carbon atoms ($C_{1-2}$ alkyl). Specifically, methyl, ethyl, propyl, isopropyl, butyl, isobutyl, sec-butyl, tert-butyl, pentyl, 2-methylbutyl, 2-methylpentyl, neopentyl, 1-ethylpropyl, hexyl, 1-methylpentyl, 3,3-dimethylbutyl, 2,2-dimethylbutyl or 1,1-dimethylbutyl may be mentioned. Among them, methyl is most preferred.

A "halogen atom" in the formula (I) is a fluorine atom, a chlorine atom, a bromine atom or an iodine atom, preferably a fluorine atom, a chlorine atom or a bromine atom. In $R^2$, a chlorine atom or a bromine atom is further preferred, and in other substituents, a fluorine atom or a chlorine atom is further preferred. And, in $R^3$, a chlorine atom is most preferred, and in other substituents, a fluorine atom is most preferred.

"$C_{1-6}$ alkoxy" in the formula (I) is linear or branched alkoxy having from 1 to 6 carbon atoms, preferably linear or branched alkoxy having from 1 to 4 carbon atoms ($C_{1-4}$ alkoxy), further preferably linear or branched alkoxy having from 1 to 3 carbon atoms ($C_{1-3}$ alkoxy), most preferably linear alkoxy having 1 or 2 carbon atoms ($C_{1-2}$ alkoxy). Specifically, methoxy, ethoxy, isopropoxy, tert-butoxy or hexyloxy may be mentioned. Among them, methoxy is most preferred.

The compound of the above formula (I) may form a salt with an acidic material or a basic material. The salt with an acidic material may be an inorganic salt such as a hydrochloride, a hydrobromide, a phosphate, a sulfate or a nitrate, and the salt with a basic material may be an inorganic or organic base salt such as a sodium salt, a potassium salt, a calcium salt, an ammonium salt or a dimethylamine salt.

The compound of the above formula (I) or its salt can be produced in accordance with a method disclosed in the above Patent Document 1 or 2.

Now, some examples of the pyridine compound preferred as an active ingredient of the pesticidal composition of the present invention will be exemplified, but it should be understood that the present invention is by no means limited thereto.

(1) At least one compound selected from the group consisting of N-cyanomethyl-4-trifluoromethyl-3-pyridinecarboxyamide (common name: flonicamid), N-(5-isoxazolyl)-4-(trifluoromethyl)nicotinamide, N-(3-methyl-5-isoxazolyl)-4-(trifluoromethyl)nicotinamide, N-(4-chloro-5-isoxazolyl)-4-(trifluoromethyl)nicotinamide, N-(4-bromo-5-isoxazolyl)-4-(trifluoromethyl)nicotinamide, N-(4-methyl-5-isoxazolyl)-4-(trifluoromethyl)nicotinamide, N-(4-ethyl-5-isoxazolyl)-4-(trifluoromethyl)nicotinamide and N-(4-methoxy-5-isoxazolyl)-4-(trifluoromethyl)nicotinamide.

(2) At least one compound selected from the group consisting of N-cyanomethyl-4-trifluoromethyl-3-pyridinecarboxyamide, N-(5-isooxazolyl)-4-(trifluoromethyl)nicotinamide, N-(3-methyl-5-isoxazolyl)-4-(trifluoromethyl) nicotinamide and N-(4-methyl-5-isoxazolyl)-4-(trifluoromethyl)nicotinamide.

(3) N-cyanomethyl-4-trifluoromethyl-3-pyridinecarboxyamide.

The nonionic surface active agent to be used as a potency-enhancing component in the present invention may, for example, be a silicone surface active agent; a polyoxyethylenealkylphenyl ether; a polyoxyethylene fatty acid ester; a formalin condensate of a polyoxyethylenealkylphenyl ether; a polyoxyethylenealkyl ether; a sorbitan higher fatty acid ester surface active agent; a polyoxyethylenearyl ether; a polyoxyethylene (mono, di or tri)phenylphenyl ether; a polyoxyethylene(mono, di or tri)benzylphenyl ether; a polyoxypropylene(mono, di or tri)benzylphenyl ether; a polyoxyethylene(mono, di or tri)styrylphenyl ether; a polyoxypropylene(mono, di or tri)styrylphenyl ether; a polymer of a polyoxyethylene(mono, di or tri)styrylphenyl ether; a polyoxyethylene polyoxypropylene block polymer; an alkylpolyoxyethylene polyoxypropylene block polymer ether; an alkylphenylpolyoxyethylene polyoxypropylene block polymer ether; a polyoxyethylene bisphenyl ether; a polyoxyethylene resin acid ester; glycerol fatty acid ester ethylene oxide adduct; castor oil ethylene oxide adduct; hydrogenated castor oil ethylene oxide adduct; an alkylamine ethylene oxide adduct and a fatty acid amide ethylene oxide adduct; a polyoxyethylene fatty acid amide; an alkylphenoxypolyethoxyethanol and polyoxyethylene rhodine ester; or an acetylene type surface active agent such as acetylene glycol or its ethylene oxide adduct, acetylene alcohol or its ethylene oxide adduct.

The above-mentioned silicone surface active agent may, for example, be tradename KF-640 (polyoxyethylene methyl polysiloxane, manufactured by Shin-Etsu Chemical Co., Ltd.), tradename DyneAmic (manufactured by STERE CHEMICAL), tradename KINETIC (polyalkylene modified polymethylsiloxane nonionic surface active agent, manufactured by STERE CHEMICAL), Silwet L-77 polyalkylene oxide-modified methylpolysiloxane, manufactured by Witco), or tradename SLIPPA (mixture of silicone polyalkylene oxide-modified methylpolysiloxane and a straight chain alcohol surface active agent, manufactured by INTERAGRO). These silicone surface active agents are distinguished from a silicone for a defoaming agent to be added in a small amount to a pesticidal composition.

The above polyoxyethylenealkylphenyl ether may, for example, be tradename Alsoap 30 (containing 30% of polyoxyethylenenonylphenyl ether, manufactured by Sumitomo Chemical Co., Ltd.), tradename Agral 30 (manufactured by ICI), tradename Agral 90 (manufactured by ICI), tradename Agral PLUS (manufactured by ICI), tradename ARKOPAL N-100 (manufactured by Hoechst AG), tradename CITOWETT (manufactured by BASF), tradename Genapol X-60, tradename KUSARINO (manufactured by NIHON NOYAKU CO., LTD.), tradename Noigen EA110 (manufactured by Dai-ichi Kogyo Seiyaku Co., Ltd.), or tradename MIX POWER (40% of polyoxyethylenealkylphenyl ether and 40% of polyoxyethylenealkyl ether, manufactured by Tomono Agrica Co., Ltd.).

The above polyoxyethylenealkyl ether may, for example, be tradename Noigen TDS-70 (manufactured by Dai-ichi Kogyo Seiyaku Co., Ltd.).

The above polyoxyethylene fatty acid ester may, for example, be tradename Lamigen ES-70 (manufactured by Dai-ichi Kogyo Seiyaku Co., Ltd.), tradename EMULAN PS700 (manufactured by BASF), tradename Pangard KS-20 (manufactured by Mitsui Toatsu Noyaku Co., Ltd.), tradename Spray Sticker (manufactured by NIHON NOYAKU CO., LTD.), tradename D-3605 (manufactured by TAKEMOTO OIL & FAT Co., Ltd.), D-230 (manufactured by TAKEMOTO OIL & FAT Co., Ltd.), tradename D-233 N (manufactured by TAKEMOTO OIL & FAT Co., Ltd.) or tradename Noigen ET-120E (manufactured by Dai-ichi Kogyo Seiyaku Co., Ltd.).

The above sorbitan higher fatty acid ester surface active agent may, for example, be tradename APPLAUCH BI (containing 50% of polyoxyethylene hexitan fatty acid ester, manufactured by Kao Corporation), tradename TWEEN 20 (fatty acid polyoxyethylene sorbitan ester, manufactured by Wako Pure Chemical Industries, Ltd.) or tradename Solgen 40 (sorbitan fatty acid ester, manufactured by Dai-ichi Kogyo Seiyaku Co., Ltd.).

The anionic surface active agent to be used as a potency-enhancing component of the present invention may, for example, be a sulfonic acid type surface active agent, a carboxylic acid type surface active agent, a sulfuric acid ester type surface active agent or a phosphoric acid ester type surface active agent.

The sulfonic acid type surface active agent may, for example, be a polyarylalkane sulfonic acid salt; a dialkylsulfosuccinic acid salt such as New Kalgen EP-70G (manufactured by TAKEMOTO OIL & FAT Co., Ltd.) or New Kalgen EX-70 (manufactured by TAKEMOTO OIL & FAT Co., Ltd.); a dialkylsulfosuccinic acid; an alkylbenzene sulfonic acid; an α-olefin sulfonic acid; a polyoxyethylenealkylphenyl ether sulfonic acid; a polyoxyethylenealkyl ether sulfosuccinic acid half ester; a naphthalene sulfonic acid and an alkylnaphthalene sulfonic acid; a dodecylbenzene sulfonic acid diethanolamine salt such as tradename EXTRAVON 40 (manufactured by Chiba-Geigy); or salts thereof.

The above carboxylic acid type surface active agent may, for example, be a polyacrylic acid, a polymethacrylic acid, a polymaleic acid, a copolymer of maleic acid with an olefin (such as isobutylene, diisobutylene, etc.) a copolymer of acrylic acid with itaconic acid, a copolymer of methacrylic acid with itaconic acid, a copolymer of maleic acid with styrene, a copolymer of acrylic acid with methacrylic acid, a copolymer of acrylic acid with methyl acrylate, a copolymer of acrylic acid with vinyl acetate, a copolymer of acrylic acid with maleic acid, or salts thereof.

The above sulfuric acid ester type surface active agent may, for example, be a higher alcohol sulfuric acid ester salt such as tradename Monogen Y-100 (manufactured by Daiichi Kogyo Seiyaku Co., Ltd.), a mixture of an alkyl sulfate and magnesium sulfate, such as tradename TRADER Pro (manufactured by COMTORIR COMMERCIAL DES LUBRIFIANTS), a polyoxyethylenealkyl ether sulfuric acid ester, a polyoxyethylenealkylphenyl ether sulfuric acid ester, a sulfuric acid ester of a polymer of a polyoxyethylenealkylphenyl ether, a polyoxyethylenebenzylphenyl ether sulfuric acid ester, a polyoxyethylenestyrylphenyl ether sulfuric acid ester, a sulfuric acid ester of a polymer of a polyoxyethylenestyrylphenyl ether, a sulfuric acid ester of a polyoxyethylene polyoxypropylene block polymer, a sulfated olefin, or salts thereof.

The above phosphoric acid ester type surface active agent may, for example, be a polyoxyethylenealkyl ether phosphoric acid ester, a polyoxyethylenealkylphenyl ether phosphoric acid ester, a phosphoric acid ester of a polymer of a polyoxyethylenealkylphenyl ether, a polyoxyethylenebenzylphenyl ether phosphoric acid ester, a polyoxyethylenestyrylphenyl ether phosphoric acid ester, a phosphoric acid ester of a polymer of a polyoxyethylenestyrylphenyl ether, a phosphoric acid ester of a polyoxyethylene polyoxypropylene block polymer or salts of such phosphoric acid esters.

Further, in the present invention, a mixture of a nonionic surface active agent and an anionic surface active agent may also be used, such as tradename Grameen S (containing 15% of a polyoxyethylenenonylphenyl ether, 5% of a polyoxyethylene fatty acid ester and 4% of sodium polynaphthylmethane sulfonate, manufactured by SANKYO AGRO CO., LTD.).

The cationic surface active agent to be used as a potency-enhancing component of the present invention may, for example, be an ethoxylated fatty acid amine surface active agent; a dialkyl ammonium salt and an alkylammonium. Specific examples of the ethoxylated fatty acid amine surface active agent include, for example, an ethoxylated tallow amine type such as tradename Frigate (manufactured by ISK Biotech Co., Ltd.), tradename Ethylan TT-15, tradename Genamin T-150 (manufactured by Hoechst AG), tradename Genamin T-200 (manufactured by Hoechst AG), tradename Ethomeen T-25, tradename Sorpol 7553 (manufactured by Toho Chemical Industry Co., Ltd.), tradename Sorpol 7409 (manufactured by Toho Chemical Industry Co., Ltd.) or tradename New Kalgen D-3615 T, and an ethoxylated soybean amine type such as tradename Sorpol 7721 (manufactured by Toho Chemical Industry Co., Ltd.), tradename New Kalgen D-3605 (manufactured by TAKEMOTO OIL & FAT Co., Ltd.), an ethoxylated coconut type such as tradename Sorpol 7376 (manufactured by Toho Chemical Industry Co., Ltd.), tradename New Kalgen D-3110 (manufactured by TAKEMOTO OIL & FAT Co., Ltd.) or tradename Ethomeen C-12. Here, Ethylan TT-15, Ethomeen T-25 and C-12 are disclosed in Weed Research, Vol. 20, p. 139-146, 1980. Further, Ethylan TT-15 is disclosed also in Zizaniology, Vol. 2, p. 183-189, 1990. A specific example of the dialkylammonium salt may, for example, be tradename NEEDS (containing 18% of dialkyldimethylammonium polynaphthylmethane sulfonate and 44% of a polyoxyethylene fatty acid ester, manufactured by Kao Corporation.

The amphoteric surface active agent to be used as a potency-enhancing component in the present invention may, for example, be a betaine type surface active agent or an amino acid type surface active agent.

The animal or plant oil to be used as a potency-enhancing component in the present invention may, for example, be a plant oil such as corn oil, soybean oil, linseed oil, sunflower oil, cotton oil, rapeseed oil, an esterified rapeseed oil such as tradename Phase II (manufactured by Loveland INDUSTRIES LTD.), olive oil, castor oil, palm oil or avocado oil; or an animal oil such as tallow or whale oil. Further, the animal or plant oil includes an extract from an animal or plant oil such as tradename Heli 700 (containing rapeseed oil phosphonolipid) or a methylated plant oil. These animal or plant oils may be used alone or in combination as a mixture of two or more of them.

The mineral oil to be used as a potency-enhancing component in the present invention may, for example, be machine oil, heavy oil, silicone oil, naphthene solvent, methyl naphthalene or 1-phenyl-1-xylylethane. These mineral oils may be used alone or in combination as a mixture of two or more of them.

The water-soluble polymer to be used as a potency-enhancing component in the present invention is not particularly limited so long as it is a polymer completely soluble or partly soluble in water, and it may, for example, be a natural water-soluble polymer such as starch, dextrin, cellulose, methylcellulose, ethylcellulose, carboxymethylcellulose, hydroxyethylcellulose, hydroxypropylcellulose, carboxymethyl starch, pullulan, sodium alginate, ammonium alginate, alginic acid propylene glycol ester, guar gum, locust bean gum, arabia gum, xanthane gum, gelatin, casein or glue; or a synthetic water-soluble polymer such as polyvinyl alcohol, polyethylene oxide, polyethylene glycol, ethylene/propylene block polymer, sodium polyacrylate or polyvinyl pyrolidone. Such water-soluble polymers may be used alone or in combination as a mixture of two or more of them. Among the water-soluble polymers, preferred are dextrin, carboxymethylcellulose and polyvinyl pyrolidone.

The resin to be used as a potency-enhancing component in the present invention may, for example, be a synthetic latex such as tradename Heli 103, an acrylic resin, a vinyl acetate resin, a vinyl chloride resin, a urethane resin, a styrene/acrylic copolymer resin, a styrene/acrylate copolymer resin, a vinyl acetate copolymer resin, a vinyl acetate/ethylene copolymer resin, a vinyl acetate/acrylic copolymer resin, a vinyl acetate/ethylene/acrylic copolymer resin or a vinyl acetate/ethylene/vinyl chloride copolymer resin. These resins may be used alone or in combination as a mixture of two or more of them. Further, in an actual use, it is preferably used in the form of an emulsion. Among such resins, a vinyl acetate resin and an urethane resin are preferred.

The wax to be used as a potency-enhancing component in the present invention may, for example, be paraffin wax, microcrystalline wax, carnauba wax, polyethylene wax or montan wax. These waxes may be used alone or in combination as a mixture of two or more of them. Further, in an actual use, it is preferably employed in the form of an emulsion. Among such waxes, microcrystalline wax, montan wax and polyethylene wax are preferred.

The pesticidal composition of the present invention may be prepared by mixing respective components and then formulating the resultant mixture, or may be prepared by formulating respective components and then mixing the resultant formulations.

The pesticidal composition of the present invention achieves pesticidal effects against various pest including anthropods such as agriculturally noxious insects, mites and the like; nematodes; and soil insects; or various diseases.

Thus, the pesticidal composition of the present invention is useful as pesticides, for example, insecticides, miticides, nematicides, soil pesticides and fungicides. For instance, it is effective against anthropods including plant parasitic mites such as two-spotted spider mite (*Tetranychus urticae*), carmine spider mite (*Tetranychus cinnabarinus*), citrus red mite (*Panonychus citri*) or bulb mite (*Rhizoglyphus echinopus*); aphids such as green peach aphid (*Myzus persicae*) or cotton aphid (*Aphis gossypii*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic insect pests such as cockroaches or housefly (*Musca domestica*); stored grain insects pests such as angoumois grain moth (*Sitotroga cerealella*), azuki bean weevil (*Callosobruchus chinensis*), confused flour beetle (*Tribolium confusum*) or mealworms; clothers insect pests such as casemaking clothes moth (*Tinea pellionella*), or black carpet beetle (*Anthrenus scrophularidae*); or household goods insect such as termites; and it is also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus lignicolus*). Furthermore, it is effective also against the soil pests. Here, the soil pests include gastropods such as slugs or snails, or isopods such as pillbugs or sowbugs. Further, it is effective against insect pests having acquired resistance to organophosphorus, carbamate and/or synthetic pyrethroid insecticides. Moreover, the composition of the present invention has excellent systemic properties, and by the application of the composition of the present invention to soil treatment, not only soil noxious insects, plant parasitic noxious mites, noxious nematodes, noxious gastropods and noxious isopods in soil but also foliage pests can be controlled.

In the same manner as in a case of conventional agricultural chemicals, the pesticidal composition in the present invention may be blended with various adjuvants and formulated into various formulations such as a soluble concentrate, an oily suspension, a wettable powder, a water soluble powder, water dispersible granule, an emulsifiable concentrate, dusts, granules and an aqueous suspension. Among them, it is preferably formulated into a solution, an oily suspension, a wettable powder, a water soluble powder or a water dispersible granule. At that time, the compound of the formula (I) or its salt and the above-described potency-enhancing component may be mixed and formulated together, or they may be separately formulated and then mixed. In an actual use of such a formulated product, it may be used as it is, or may be used as diluted to a predetermined concentration with a diluting agent such as water. Here, the adjuvants may, for example, be a carrier, a dispersing agent, an emulsifying agent, a suspension agent, a thickener, a stabilizer, a moistening agent, a penetrating agent, an antifreezer, an antifoaming agent, etc., and they may suitably be added, as the case requires.

The above carriers may be classified into solid carriers and liquid carriers. The solid carriers may, for example, be powders of animal and plant origin such as starch, sugar, lactose, cellulose powder, cyclodextrin, activated carbon, soybean flour, wheat flour and powdered milk; or mineral powders such as talc, kaolin, bentonite, organic bentonite, calcium carbonate, calcium sulfate, sodium bicarbonate, zeolite, diatomaceous earth, white carbon, clay, alumina and silica. The liquid carriers may, for example, be water; alcohols such as ethyl alcohol and ethylene glycol; ketones such as acetone, methyl ethyl ketone, methyl isobutyl ketone and isophorone; ethers such as dioxane and tetrahydrofuran; aliphatic hydrocarbons such as kerosine, coal oil and liquid paraffin; aromatic hydrocarbons such as xylene, trimethylbenzene, tetramethylbenzene, cyclohexane and solvent naphtha; acid amides such as N,N-dimethylformamide and N,N-dimethylacetamide; esters such as ethylacetate ester and glycerin ester of a fatty acid; nitriles such as acetonitrile; sulfur-containing compounds such dimethylsulfoxide, and N-methyl-2-pyrolidone.

The above-mentioned water-soluble polymer as a part of the potency-enhancing component or some surfactant such as tradename Dixzol (manufactured by Dai-ichi Kogyo Seiyaku Co., Ltd.) acts also as a dispersing agent. However, another dispersing agent such as a surfactant/silica blended product, a sodium alkylnaphthalene sulfonate/formaldehyde condensate or ammonium sulfate may also be used. Further, as the emulsifying agent, various ones may be employed, but one acting as an emulsifying agent among nonionic surface active agents or anionic surface active agents as a part of the above potency-enhancing component may also be used.

In a case where the pesticidal composition in the present invention is formulated into a soluble concentrate, the above-mentioned liquid carrier is employed in addition to the pyridine compound of the formula (I) or its salt and the potency-enhancing component. In such a case, a proper mixing ratio of the compound of the formula (I) or its salt to the liquid carrier is usually from 1:500 to 1:1, preferably from 1:50 to 1:1, by weight ratio.

In a case where the pesticide composition in the present invention is formulated in the form of an oily suspension, it is necessary to use at least one oily potency-enhancing component selected from the group consisting of a mineral oil, an animal oil and a wax, as the potency-enhancing component. In such a case, a proper mixing ratio of the compound of the formula (I) or its salt to the oily potency-enhancing component is usually from 1:500 to 2:1, preferably from 1:50 to 1:1, by weight ratio.

In a case where the pesticidal composition in the present invention is formulated in the form of a wettable powder, the above-mentioned solid carrier and dispersing agent are used in addition to the pyridine compound of the formula (I) or its salt and the above potency-enhancing component. In such a case, a proper mixing ratio of the compound of the formula (I) or its salt to the solid carrier is usually from 1:500 to 100:1, preferably from 1:50 to 20:1, by weight ratio. Further, a proper mixing ratio of the compound of the formula (I) or its salt to the dispersing agent is usually from 1:10 to 100:1, preferably from 1:2 to 50:1, by weight ratio.

In a case where the pesticidal composition in the present invention is formulated in the form of a water soluble powder, the above mentioned solid carrier and dispersing agent are used in addition to the pyridine compound of the formula (I) or its salt and the above potency-enhancing component. In such a case, a proper mixing ratio of the compound of the formula (I) or its salt to the solid carrier is usually from 1:500 to 100:1, preferably from 1:50 to 20:1, by weight ratio. Further, a proper mixing ratio of the compound of the formula (I) or its salt to the dispersing agent is usually from 1:10 to 100:1, preferably from 1:2 to 50:1, by weight ratio.

In a case where the pesticidal composition in the present invention is formulated in the form of the water soluble granule, the above-mentioned solid carrier and dispersing agent are used in addition to the pyridine compound of the formula (I) or its salt and the above potency-enhancing component. In such a case, a proper mixing ratio of the compound of the formula (I) or its salt to the solid carrier is usually from 1:500 to 100:1, preferably from 1:50 to 20:1, by weight ratio. Further, a proper mixing ratio of the compound of the formula (I) or its salt to the dispersing agent is usually from 1:10 to 100:1, preferably from 1:2 to 50:1, by weight ratio.

The pesticidal composition in the present invention may be used in combination with or as mixed with other agricultural chemicals, such as fungicides, insecticides, miticides, nematicides, soil pesticides, antiviral agents, attractants, herbicides or plant growth regulators, as the case requires. In such a case, further improved effects may sometimes be obtainable.

The fungicidal active compounds in the above-mentioned other agricultural chemicals include, for example, (by common names, some of them are still in an application stage, or test codes of Japan Plant Protection Association) anilinopyrimidine compounds such as mepanipyrim, pyrimethanil, cyprodinil and ferimzone; a triazoropyrimidine compound such as 5-chloro-7-(4-methylpiperidin-1-yl)-6-(2,4,6-trifluorophenyl)-[1,2,4]triazolo[1,5-a]pyrimidine; pyridinamine compounds such as fluazinam; azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole; quinoxaline compounds such as quinomethionate; dithiocarbamate compounds such as maneb, zineb, mancozeb, polycarbamate, metiram, propineb and thiram; organic chlorine compounds such as fthalide, chlorothalonil and quintozene, imidazole compounds such as benomyl, thiophanate-methyl, carbendazim, thiabendazole, fuberiazole and cyazofamid; cyanoacetamide compounds such as cymoxanil; phenylamide compounds such as metalaxyl, metalaxyl-M, mefenoxam, oxadixyl, ofurace, benalaxyl, benalaxyl-M (another name: kiralaxyl, chiralaxyl), furalaxyl and cyprofuram; sulfenic acid compounds such as dichlofluanid; copper compounds such as cupric hydroxide and oxine copper; isoxazole compounds such as hymexazol; organophosphorus compounds such as fosetyl-Al, tolclofos-methyl, S-benzyl, O,O-diisopropylphosphorothioate, O-ethyl, S,S-diphenylphosphorodithioate and aluminum ethylhydrogen phosphonate, edifenphos, iprobenfos; N-halogenothioalkyl compounds such as captan, captafol and folpet; dicarboximide compounds such as procymidone, iprodione and vinclozolin; benzanilide compounds such as flutolanil, mepronil, zoxamid and tiadinil; anilide compounds such as carboxin, oxycarboxin, thifluzamide, penthiopyrad, boscalid, bixafen, fluopyram, isotianil and mixture of 2 syn-isomers 3-(difluoromethyl)-1-methyl-N[(1RS,4SR,9SR)-1,2,3,4-tetrahydro-9-isopropyl-1,4-methanonaphthalen-5-yl]pyrazole-4-carboxamide and 2-anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (isopyrazam); piperazine compounds such as triforine; pyridine compounds such as pyrifenox; carbinol compounds such as fenarimol and flutriafol; piperidine compounds such as fenpropidine, morpholine compounds such as fenpropimorph, spiroxamine and tridemorph; organotin compounds such as fentin hydroxide and fentin acetate; urea compounds such as pencycuron; cinnamic acid compounds such as dimethomorph and flumorph; phenylcarbamate compounds such as diethofencarb, cyanopyrrole compounds such as fludioxonil and fenpiclonil; strobilurin compounds such as azoxystrobin, kresoxim-methyl, metominofen, trifloxystrobin, picoxystrobin, oryzastrobin, dimoxystrobin, pyraclostrobin, and fluoxastrobin; oxazolidinone compounds such as famoxadone, thiazolecarboxamide compounds such as ethaboxam; silylamide compounds such as silthiopham; aminoacid amidecarbamate compounds such as iprovalicarb and valiphenal; benthiavalicarb-isopropyl; imidazolidine compounds such as fenamidone; hydroxanilide compounds such as fenhexamid; benzenesulfonamide compounds such as flusulfamide; oxime ether compounds such as cyflufenamid; phenoxyamide compounds such as fenoxanil; antibiotics such as validamycin, kasugamycin and polyoxins; guanidine compounds such as iminoctadine and dodine; 4-quinolionol derivative compounds such as 2,3-dimethyl-6-t-butyl-8-fluoro-4-acetylquinoline; cyanomethylene compounds such as 2-(2-fluoro-5-(trifluoromethyl)phenylthio)-2-(3-2-methoxyphenyl)thiazolidin-2-yliden)acetonitrile; and other compounds such as pyribencarb, isoprothiolane, Pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), mandipropamid, fluopicolide, carpropamid, and meptyldinocap.

The active compounds of insect pest control agents such as insecticides, miticides, nematicides or soil pesticides in the above-mentioned other agricultural chemicals, include, for example, (by common names, some of them are still in an application stage, or test codes) organic phosphate compounds such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, paration, phosphocarb, demeton-S-methyl, monocrotophos, methamidophos, imicyafos, parathion-methyl, terbufos, phospamidon, phosmet and phorate; carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb; nereistoxin derivatives such as cartap, thiocyclam, bensultap and thiosultap-sodium; organic chlorine compounds such as dicofol, tetradifon, endosulufan, dienochlor and dieldrin; organic metal compounds such as fenbutatin Oxide and cyhexatin, pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, imidate and flumethrin; benzoylurea compounds such as diflubenzuron, chlorfluazuron, teflubenzuron, flufenoxuron, triflumuron, hexaflumuron, lufenuron, novaluron, noviflumuron, bistrifluoron and fluazuron; juvenile hormone-like compounds such as methoprene, pyriproxyfen, fenoxycarb and diofenolan; pyridazinone compounds such as pridaben; pyrazole compounds such as fenpyroximate, fipronil, tebufenpyrad, ethiprole, tolfenpyrad, acetoprole, pyrafluprole and pyriprole; neonicotinoids such as imidacloprid, nitenpyram, acetamiprid, thiacloprid, thiamethoxam, clothianidin, nidinotefuran, dinotefuran and nithiazine; hydrazine compounds such as tebufenozide, methoxyfenozide, chromafenozide and halofenozide; pyridine compounds such as pyridaryl and flonicamid; tetronic acid compounds such as spirodiclofen; strobilurin compounds such as fluacrypyrim; pyridinamine compounds such as flufenerim; dinitro compounds; organic sulfur compounds; urea compounds; triazine compounds; hydrazone compounds; and other compounds such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazon, fenazaquin, pyridaben, amidoflumet, chlorobenzoate, sulfluramid, hydramethylnon, metaldehyde, HGW 86, ryanodine, flufenrim, pyridalyl, spirodiclofen, verbutin, thiazolylcinnanonitrile, amidoflumet, AKD-1022, IKA-2000, and the like. Further, microbial agricultural chemicals such as *Bacillus* thuringienses aizawai, *Bacillus thuringienses kurstaki, Bacillus thuringienses israelensis, Bacillus thuringienses japonensis, Bacillus thuringienses tenebrionis*, insecticidal crystal protein produced by *Bacillus thuringienses*, insect viruses, etomopathogenic fungi, and nematophagous fungi; antibiotics or semisynthetic antibiotics such as avermectin, emamectinbenzoate, milbemectin, milbemycin, spinosad, ivermectin, lepimectin, DE-175, abamectin and emamectin and spinetoram; natural products such as azadirachtin and rotenone; and repellents such as deet may, for example, be mentioned.

In the pesticidal composition of the present invention, a proper mixing ratio of the compound of the formula (I) or its salt to the potency-enhancing component is usually from 1:1,000 to 100:1, preferably from 1:100 to 10:1, more preferably from 1:50 to 4:1, most preferably from 1:20 to 2:1, by weight ratio.

The practical concentration of the pesticidal composition of the present invention cannot be generally defined since it varies depending upon the condition such as the objective crop plant, the method of use, the type of formulation, the applied amount, etc. However, in the case of foliage treatment, the concentration of the active ingredient is usually from 1 to 1,000 ppm, and the concentration of the potency-enhancing component is from 1 to 10,000 ppm. In the case of soil treatment, the concentration of the active ingredient is usually from 0.01 to 10 kg/ha, and the concentration of the potency-enhancing component is from 0.1 to 10 kg/ha.

A preferred embodiment of the method for controlling pests of the present invention may be a method wherein the pesticidal composition of the present invention is applied to pests in the form of an aqueous dispersion. In this method, the pesticidal composition in the form of an aqueous dispersion is applied to a site where pests germinate or expected to germinate. As such a site, the foliage of an agricultural or horticultural plant, soil, etc. may be mentioned, and in the case of the foliage of an agricultural or horticultural plant, the application is particularly effective. The aqueous dispersion may be one prepared by dispersing a formulated product of the active ingredient in water and adding the potency-enhancing component thereto; one prepared by dispersing in water a formulation which is preliminarily prepared by mixing the active ingredient and the potency-enhancing component; or one prepared by dispersing in water by a method similar to such methods. At the time of applying the aqueous dispersion, the aqueous dispersion is prepared and used with water in an amount of 1 L to from 0.1 to 10,000 mg of the pesticidal composition. The aqueous dispersion is prepared so that the concentration of the active ingredients will be from 0.1 to 10,000 ppm. The amount of the aqueous dispersion to be applied is from 100 to 10,000 L per 1 ha. As the aqueous dispersion, an aqueous suspension formulation may be employed. Such an aqueous suspension formulation is prepared so that the concentration of the active ingredient will be from 0.1 to 10,000 ppm. The amount of the aqueous suspension formulation to be applied is from 100 to 10,000 L per 1 ha.

Now, some preferred embodiments of the pesticidal composition of the present invention will be exemplified, but it should be understood that the present invention is by no means thereby restricted.

(1) A pesticidal composition comprising the pyridine compound or its salt, and at least one potency-enhancing component selected from the group consisting of a nonionic surface active agent, an anionic surface active agent, a cationic surface active agent, an amphoteric surface active agent, an animal or plant oil, a mineral oil, a water-soluble polymer, a resin and a wax.

(2) The pesticidal composition according to (1), wherein the potency-enhancing component is at least one member selected from the group consisting of a nonionic surface active agent, an anionic surface active agent, a cationic surface active agent, an amphoteric surface active agent, an animal or plant oil and a resin.

(3) The pesticidal composition according to (1) or (2), wherein the nonionic surface active agent is a silicone surface active agent, a polyoxyethylenealkylphenyl ether, a polyoxyethylene fatty acid ester, a formalin condensate of a polyoxyethylenealkylphenyl ether, a polyoxyethylene alkyl ether, a sorbitan higher fatty acid ester surface active agent, a polyoxyethylenearyl ether, a polyoxyethylene(mono, di or tri)phenylphenyl ether, a polyoxyethylene(mono, di or tri)benzylphenyl ether, a polyoxypropylene(mono, di or tri)benzylphenyl ether, a polyoxyethylene(mono, di or tri)styrylphenyl ether, a polyoxypropylene(mono, di or tri)styrylphenyl ether, a polymer of a polyoxyethylene(mono, di or tri)styrylphenyl ether, a polyoxyethylene polyoxypropylene block polymer, an alkylpolyoxyethylene polyoxypropylene block polymer ether, an alkylphenylpolyoxyethylene polyoxypropylene block polymer ether, a polyoxyethylenebisphenyl ether, a polyoxyethylene resin acid ester, a glycerol fatty acid ester ethylene oxide adduct, a castor oil ethylene oxide adduct, hydrogenated castor oil ethylene oxide adduct, an alkylamine ethylene oxide adduct and a fatty acid amide ethylene oxide adduct, a polyoxyethylene fatty acid amide, an alkylphenoxypolyethoxyethanol and polyoxyethylene rhodine ester, or an acetylene type surface active agent.

(4) The pesticidal composition according to (1) or (2), wherein the nonionic surface active agent is a silicone surface active agent, a polyoxyethylenealkylphenyl ether or a polyoxyethylene fatty acid ester.

(5) The pesticidal composition according to (1) or (2), wherein the anionic surface active agent is a sulfonic acid type surface active agent, a carboxylic acid type surface active agent, a sulfuric acid ester type surface active agent or a phosphoric acid ester type surface active agent.

(6) The pesticidal composition according to (1) or (2), wherein the anionic surface active agent is a sulfonic acid type surface active agent.

(7) The pesticidal composition according to (1) or (2), wherein the cationic surface active agent is an ethoxylated aliphatic amine surface active agent, a dialkylammonium salt or an alkylammonium.

(8) The pesticidal composition according to (1) or (2), wherein the cationic surface active agent is an ethoxylated aliphatic amine surface active agent or a dialkylammonium salt.

(9) The pesticidal composition according to (2), wherein the potency-enhancing component is at least one member selected from the group consisting of a silicone surface active agent, a polyoxyethylenealkylphenyl ether, a polyoxyethylene fatty acid ester, a sorbitan higher fatty acid ester surface active agent, a sulfonic acid type surface active agent, a sulfuric acid ester type surface active agent, an ethoxylated aliphatic amine surface active agent, a dialkylammonium salt, an animal or plant oil and a synthetic latex.

(10) The pesticidal composition according to (9), wherein the potency-enhancing component is a silicone surface active agent.

(11) The pesticidal composition according to (1) to (10), which contains, in addition to the pyridine compound or its salt and the potency-enhancing component, a liquid carrier, and which is formulated into a soluble concentrate.

(12) The pesticidal composition according to (1) to (10), which contains, as the potency-enhancing agent, at least one member selected from the group consisting of a mineral oil, an animal oil and a wax, and which is formulated into an oily suspension.

(13) The pesticidal composition according to (1) to (10), which contains, in addition to the pyridine compound or its salt and the potency-enhancing component, a solid carrier and a dispersing agent, and which is formulated into a wettable powder.

(14) The pesticidal composition according to (1) to (10), which contains, in addition to the pyridine compound or its salt and the potency-enhancing component, a solid carrier and a dispersing agent, and which is formulated into a water soluble powder.

(15) The pesticidal composition according to (1) to (10), which contains, in addition to the pyridine compound or its salt and the potency-enhancing component, a solid carrier and a dispersing agent, and which is formulated into a water soluble granule.

(16) The pesticidal composition according to (1) to (15), wherein the mixing weight ratio of the pyridine compound or its salt to the potency-enhancing component is from 1:1000 to 100:1.

(17) A method for controlling pests, which comprises applying the pesticidal composition as defined in (1) to pests.

(18) A method for enhancing the pesticidal potency of a pyridine compound represented by the above formula (I) or its salt by at least one potency-enhancing component selected from the group consisting of a nonionic surface active agent, an anionic surface active agent, a cationic surface active agent, an amphoteric surface active agent, an animal or plant oil, a mineral oil, a water-soluble polymer, a resin and a wax.

EXAMPLES

Test Example 1 (Test on Effects Against Green Peach Aphid (*Myzus persicae*))

The numbers of apterous adults and nymphs of green peach aphid parasitized on a 7- to 8-foliate radish planted in a pot having a diameter of 10 cm, were counted, and then a pesticide solution prepared to contain flonicamid at a rate of 0.05 g/liter and contain a potency-enhancing component at a predetermined concentration, was applied by spraying at a rate of 1,000 liters/ha. After the treatment, the pot was kept in an outdoor biotron under various temperature conditions. As the time passed, the numbers of parasitic green peach aphid were counted in the same manner as above, and the controlling value was calculated by the following formula. The test was repeated twice. The results are shown in Tables 1 to 3. In Tables in this specification, "liter" is represented by "l".

By the addition of the tested potency-enhancing components to N-cyanomethyl-4-trifluoromethyl-3-pyridinecarboxyamide, the control effects were improved.

$$\text{Controlling value} = (1 - (T_a \times C_b)/(T_b \times C_a)) \times 100$$

$T_a$ = The number of insects in treated section after treatment $T_b$ = The number of insects in treated section before treatment $C_a$ = The number of insects in non-treated section after treatment $C_b$ = The number of insects in non-treated section before treatment

TABLE 1

(Table 1) Temperature in a biotron: 10° C.

| Potency-enhancing component | | | Controlling value | | | |
|---|---|---|---|---|---|---|
| Type | Tradename | Concentration | After 3 days | After 7 days | After 12 days | After 19 days |
| Animal or plant oil | Heli 700 | 2.5 ml/l | 40 | 84 | 98 | 99 |
| Synthetic latex | Heli 103 | 1.4 ml/l | 47 | 91 | 98 | 97 |
| Nil | | | 43 | 68 | 59 | 70 |

TABLE 2

(Table 2) Temperature in a biotron: 10 to 15° C.

| Potency-enhancing component | | | Controlling value | | |
|---|---|---|---|---|---|
| Type | Tradename | Concentration | After 4 days | After 10 days | After 14 days |
| Silicone surface active agent | Silwet L-77 | 0.25 ml/l | 71 | 93 | 99 |
| Silicone surface active agent | Silwet L-77 | 0.125 ml/l | 58 | 90 | 100 |
| Polyoxyethylene fatty acid ester | EMULAN PS700 | 3.5 ml/l | 82 | 96 | 99 |

TABLE 2-continued (Table 2) Temperature in a biotron: 10 to 15° C.

| Potency-enhancing component | | | Controlling value | | |
|---|---|---|---|---|---|
| Type | Tradename | Concentration | After 4 days | After 10 days | After 14 days |
| Polyoxyethylene fatty acid ester | EMULAN PS700 | 1.75 ml/l | 90 | 97 | 98 |
| Sulfonic acid type surface active agent | EXTRAVON 40 | 1.0 ml/l | 67 | 92 | 98 |
| Animal or plant oil | Heli 700 | 2.5 ml/l | 79 | 88 | 95 |
| Nil | | | 45 | 60 | 74 |

TABLE 3

(Table 3) Temperature in a biotron: 10 to 13° C.

| Potency-enhancing component | | | Controlling value | | |
|---|---|---|---|---|---|
| Type | Tradename | Concentration | After 3 days | After 7 days | After 14 days |
| Polyoxyethylenealkyl-phenyl ether | Alsoap 30 | 1.0 ml/l | 85 | 95 | 94 |
| Polyoxyethylenealkyl-phenyl ether | Agral 90 | 1.0 ml/l | 72 | 96 | 95 |
| Ethoxylated aliphatic amine surface active agent | Frigate | 1.0 ml/l | 71 | 88 | 92 |
| Dialkylammonium salt | NEEDS | 1.0 ml/l | 60 | 81 | 83 |
| Nil | | | 32 | 36 | 53 |

Test Example 2 (Test on Effects Against *Rhopalosiphum padi*)

The numbers of apterous adults and nymphs of *Rhopalosiphum padi* parasitized on wheat planted in a 1/5,000a pot were counted, and then a pesticide solution prepared to contain flonicamid at rate of 0.15 g/liter and contain a potency-enhancing component at a predetermined concentration, was applied by spraying at a rate of 200 liters/ha, and the pot was kept in a greenhouse. After the treatment, as time passed, the numbers of parasitic *Rhopalosiphum padi* were counted in the same manner as above, and the controlling value was calculated by the following formula. The test was repeated twice. The results are shown in Table 4.

By the addition of the tested potency-enhancing components to N-cyanomethyl-4-trifluoromethyl-3-pyridinecarboxyamide, the control effects were improved.

Controlling value $= (1 - (T_a \times C_b)/(T_b \times C_a)) \times 100$ $T_a$ = The number of insects in treated section after treatment $T_b$ = The number of insects in treated section before treatment $C_a$ = The number of insects in non-treated section after treatment $C_b$ = The number of insects in non-treated section before treatment

TABLE 4

(Table 4)

| Potency-enhancing component | | | Controlling value | | |
|---|---|---|---|---|---|
| Type | Tradename | Concentration | After 3 days | After 7 days | After 14 days |
| Silicone surface active agent | Silwet L-77 | 1.0 ml/l | 99 | 98 | 98 |
| Silicone surface active agent | Silwet L-77 | 0.5 ml/l | 98 | 98 | 96 |
| Silicone surface active agent | Silwet L-77 | 0.25 ml/l | 98 | 98 | 96 |
| Nil | | | 54 | 66 | 61 |

Test Example 3 (Test on Effects Against *Rhopalosiphum padi*)

The numbers of apterous adults and nymphs of *Rhopalosiphum padi* parasitized on wheat planted in a 1/5,000a pot were counted, and then a pesticide solution prepared to contain flonicamid at rate of 0.25 g/liter and contain a potency-enhancing component at a predetermined concentration, was applied by spraying at a rate of 200 liters/ha, and the pot was kept in a greenhouse. After the treatment, as time passed, the numbers of parasitic *Rhopalosiphum padi* were counted in the same manner as above, and the controlling value was calculated in the same manner as in Test Example 2. The test was repeated three times. The results are shown in Table 5.

TABLE 5

(Table 5)

| Potency-enhancing component | | | Controlling value | | |
|---|---|---|---|---|---|
| Type | Tradename | Concentration | After 2 days | After 7 days | After 17 days |
| Animal or plant oil | Phase II | 5 ml/l | 98 | 97 | 92 |
| Sulfuric acid ester type surface active agent | TRADER Pro | 1 ml/l | 92 | 96 | 93 |
| Nil | | | 88 | 95 | 88 |

Formulation Example 1: Soluble Concentrate 20.5 parts by weight of flonicamid and 33.3 parts by weight of tradename KF-640 (polyoxyethylene methyl polysiloxane, manufactured by Shin-Etsu Chemical Co., Ltd.) were dissolved in 46.2 parts by weight of N,N-dimethylacetamide to obtain a 20% soluble concentrate.

Formulation Example 2: Soluble Concentrate 10.3 parts by weight of flonicamid and 20 parts by weight of tradename New Kalgen EP-70G (sodium dioctyl sulfosuccinate, manufactured by TAKEMOTO OIL & FAT Co., Ltd.) were dissolved in 69.7 parts by weight of N,N-dimethylacetamide to obtain a 10% soluble concentrate.

Formulation Example 3: Soluble Concentrate 10.3 parts by weight of flonicamid and 20 parts by weight of tradename Noigen TDS-70 (polyoxyethylenealkyl ether, manufactured by Dai-ichi Kogyo Seiyaku Co., Ltd.) were dissolved in 69.7 parts by weight of N,N-dimethylacetamide to obtain a 10% soluble concentrate.

Formulation Example 4: Oily Suspension 5.2 parts by weight of flonicamid, 10 parts by weight of tradename Sorpol 3815K (mixture of hydrogenated castor oil ethylene oxide adduct and polyoxyethylenealkylphenyl ether, manufactured by Toho Chemical Industry Co., Ltd.), 1 part by weight of tradename New D ORBEN (organic bentonite, manufactured by SHIRAISHI KOGYO) and 83.8 parts by weight of soybean oil were wet-pulverized to obtain a 5% oily suspension.

Formulation Example 5: Wettable Powder 10.3 parts by weight of flonicamid, 10 parts by weight of tradename Dixzol W-205A (dispersing agent, manufactured by Dai-ichi Kogyo Seiyaku Co., Ltd.), 29.7 parts by weight of Kaolin, and 50 parts by weight of a blend product prepared by mixing tradename Solgen 40 (sorbitan fatty acid ester, manufactured by Dai-ichi Kogyo Seiyaku Co., Ltd.) and tradename Carplex #80 (white carbon, manufactured by Degussa) in a weight ratio of 1:1, were mixed and pulverized to obtain a 10% wettable powder.

Formulation Example 6: Water Soluble Powder 10.3 parts by weight of flonicamid, 20 parts by weight of tradename New Kalgen EX-70G (sodium dioctyl sulfosuccinate, manufactured by TAKEMOTO OIL & FAT Co., Ltd.), 5 parts by weight of tradename Morwet D-425P (sodium alkylnaphthalene sulfonate/formaldehyde condensate, manufactured by Rhodia Nicca) and 64.7 parts by weight of lactose were mixed and pulverized to obtain a 10% water soluble powder.

Formulation Example 7: Water Soluble Granule 10.3 parts by weight of flonicamid, 10 parts by weight of tradename Lamigen ES-60 (polyoxyethylene fatty acid ester, manufactured by Dai-ichi Kogyo Seiyaku Co., Ltd.), 5 parts by weight of tradename Morwet D-425P (sodium alkylnaphthalane sulfonate/formaldehyde condensate, manufactured by LION AKZO Co., Ltd.) and 74.7 parts by weight of ammonium sulfate were mixed and then water was added, followed by kneading, granulation, drying and particle size adjustment to obtain a 10% water soluble granule.

Test Example 4 (Test on Effects Against *Rhopalosiphum padi* of Formulated Product)

The numbers of apterous adults and nymphs of *Rhopalosiphum padi* parasitized on wheat planted in a 1/5,000a pot were counted, and then, a pesticide solution obtained by diluting the soluble concentrate disclosed in the above Formulation Example 1 with water so that flonicamid became 0.15 g/liter, was applied by spraying at a rate of 200 liters/ha, and the pot was kept in an outdoor biotron (20° C.). After the treatment, as the time passed, the numbers of parasitic *Rhopalosiphum padi* were counted in the same manner as above. The test was repeated three times. The results are shown in Table 6.

TABLE 6

(Table 6)

| Treating formulation | Number of parasitic *Rhopalosiphum padi* per pot ||||| 
|---|---|---|---|---|---|
| | Before treatment | After 3 days | After 7 days | After 10 days | After 14 days |
| Diluted product of the solution of Formulation Example 1 | 959.7 | 20.0 | 6.3 | 32.0 | 52.3 |
| Non-treatment | 791.7 | 846.3 | 1,197.3 | 1,540.0 | 1,686.7 |

INDUSTRIAL APPLICABILITY

The pesticidal composition of the present invention is one having the problems of conventional products solved and having stable and high pesticidal effects and can be widely used to control pests.

The entire disclosure of Japanese Patent Application No. 2008-107804 filed on Apr. 17, 2008 including specification, claims, drawing and abstract is incorporated herein by reference in its entirety.

The invention claimed is:

1. A pesticidal composition comprising N-cyanomethyl-4-trifluoromethyl-3-pyridinecarboxyamide or a salt thereof and a silicone surface active agent,
   wherein the mixing weight ratio of N-cyanomethyl-4-trifluoromethyl-3-pyridinecarboxyamide or a salt thereof to the silicone surface active agent is from 1:100 to 10:1, wherein the silicone surface active agent is polyalkylene oxide-modified methylpolysiloxane.

2. The pesticidal composition according to claim 1, which further comprises, in addition to the N-cyanomethyl-4-trifluoromethyl-3-pyridinecarboxyamide or a salt thereof and the silicone surface active agent, a liquid carrier, and which is formulated into a soluble concentrate.

3. A method for controlling pests, which comprises applying the pesticidal composition as defined in claim 1 to pests.

4. A method for enhancing the pesticidal potency of N-cyanomethyl-4-trifluoromethyl-3-pyridinecarboxyamide or a salt thereof, comprising
   combining N-cyanomethyl-4-trifluoromethyl-3-pyridinecarboxyamide or a salt thereof with a silicone surface active agent in a mixing weight ratio of N-cyanomethyl-4-trifluoromethyl-3-pyridinecarboxyamide or a salt thereof to the silicone surface active agent of 1:100 to 10:1, wherein the silicone surface active agent is polyalkylene oxide-modified methylpolysiloxane.

* * * * *